US006979723B2

(12) United States Patent
Leadbetter et al.

(10) Patent No.: US 6,979,723 B2
(45) Date of Patent: Dec. 27, 2005

(54) PROCESS FOR PREPARING GLYCOPEPTIDE PHOSPHONATE DERIVATIVES

(75) Inventors: Michael R. Leadbetter, San Leandro, CA (US); Martin S. Linsell, San Mateo, CA (US); Junning Lee, El Granada, CA (US); Jyanwei Liu, Sunnyvale, CA (US)

(73) Assignee: Theravance, Inc., South San Francisco, CA (US)

( * ) Notice: Subject to any disclaimer, the term of this patent is extended or adjusted under 35 U.S.C. 154(b) by 3 days.

(21) Appl. No.: 10/226,428

(22) Filed: Aug. 23, 2002

(65) Prior Publication Data

US 2003/0069391 A1 Apr. 10, 2003

Related U.S. Application Data

(60) Provisional application No. 60/314,831, filed on Aug. 24, 2001.

(51) Int. Cl.$^7$ .............................................. A61K 38/00
(52) U.S. Cl. ...................................................... 530/322
(58) Field of Search ........................................ 530/322

(56) References Cited

U.S. PATENT DOCUMENTS

| | | | |
|---|---|---|---|
| 3,160,632 | A | 12/1964 | Toy et al. |
| 4,643,987 | A | 2/1987 | Nagarajan et al. |
| 4,698,327 | A | 10/1987 | Nagarajan et al. |
| 5,591,714 | A | 1/1997 | Nagarajan et al. |
| 5,750,509 | A | 5/1998 | Malabarba et al. |
| 5,840,684 | A | 11/1998 | Cooper et al. |
| 5,916,873 | A | 6/1999 | Cooper et al. |
| 5,952,466 | A | 9/1999 | Berglund et al. |
| 5,998,581 | A | 12/1999 | Berglund et al. |
| 6,392,012 | B1 | 5/2002 | Judice et al. |
| 6,444,786 | B1 | 9/2002 | Judice et al. |
| 6,455,669 | B1 | 9/2002 | Judice et al. |
| 6,518,242 | B1 | 2/2003 | Chen et al. |
| 6,635,618 | B2 * | 10/2003 | Leadbetter et al. ............ 514/7 |
| 2002/0010131 | A1 | 1/2002 | Linsell |
| 2002/0022590 | A1 | 2/2002 | Leadbetter et al. |

FOREIGN PATENT DOCUMENTS

| | | |
|---|---|---|
| EP | 0 201 251 A2 | 12/1986 |
| EP | 0 376 041 B1 | 7/1990 |
| EP | 0 525 499 A1 | 2/1993 |
| EP | 0 667 353 A1 | 8/1995 |
| EP | 0 816 378 A1 | 1/1998 |
| EP | 0 873 997 A1 | 10/1998 |
| WO | WO 98/21952 | 5/1998 |
| WO | WO 99/42476 | 8/1999 |
| WO | WO 00/39156 | 7/2000 |
| WO | WO 00/59528 | 10/2000 |
| WO | WO 01/83521 A2 | 11/2001 |
| WO | WO 01/98328 A2 | 12/2001 |

OTHER PUBLICATIONS

Cooper et al., "Reductive Alkylation of Glycopeptide Antibiotics: Synthesis and Antibacterial Activity", The Journal of Antibiotics, vol. 49, No. 6, pp 575–581 ((1996).
Nagarajan et al., "Synthesis and Antibacterial Evaluation of N–Alkyl Vancomycins", The Journal of Antibiotics, vol. XLII, No. 1, pp 63–72 (1988).
Nicolaou et al., "Chemistry, Biology, and Medicine of the Glycopeptide Antibiotics", Angew Chem. Int. Ed., vol. 38, No. 15, pp 2097–2152 (1999).
Pavlov et al., "A New Type of Chemical Modification of Glycopeptides Antibiotics: Aminomethylated Derivatives of Eremomycin and Their Antibacterial Activity", The Journal of Antibiotics, vol. 50, No. 6, pp 509–513 (1997).
Pavlov et al., "Chemical Modification of Glycopeptide Antibiotics [VC1]", Russian Journal of Bioorganic Chemistry, vol. 24, No. 9, pp 570–587 (1998).
Rodriguez et al., "Novel Glycopeptide Antibiotics: N–Alkylated Derivatives Active Against Vancomycin–Resistant *Enterococci*", The Journal of Antibiotics, vol. 51, No. 6, pp 560–569 (1998).
Snyder et al., "Enzymatic Deacylation of Teicoplanin Followed by Reductive Alkylation: Synthesis and Antibacterial Activity of New Glycopeptides", The Journal of Antibiotics, vol. 51, No. 10, pp 945–951 (1998).

* cited by examiner

*Primary Examiner*—Christopher R. Tate
*Assistant Examiner*—Maury Audet
(74) *Attorney, Agent, or Firm*—Jeffrey A. Hagenath

(57) ABSTRACT

Disclosed are processes for preparing glycopeptide phosphonate derivatives having an amino-containing side chain. Several of the process steps are conducted in a single reaction vessel without isolation of intermediate reaction products, thereby generating less waste and improving the overall efficiency and yield of the process.

24 Claims, No Drawings

PROCESS FOR PREPARING GLYCOPEPTIDE PHOSPHONATE DERIVATIVES

CROSS-REFERENCE TO RELATED APPLICATIONS

This application claims the benefit of U.S. Provisional Application No. 60/314,831, filed on Aug. 24, 2001; the entire disclosure of which is incorporated herein by reference in its entirety.

BACKGROUND OF THE INVENTION

1. Field of the Invention

This invention is directed to novel processes for preparing derivatives of glycopeptide antibiotics. More specifically, this invention is directed to multi-step processes for preparing phosphonate derivatives of glycopeptide antibiotics having an amino-containing side chain, the first two steps being conducted in a single reaction vessel without isolation of the intermediate reaction products.

2. Background

Glycopeptides (e.g. dalbaheptides) are a well-known class of antibiotics produced by various microorganisms (see *Glycopeptide Antibiotics*, edited by R. Nagarajan, Marcel Dekker, Inc. New York (1994)). Many synthetic derivatives of such glycopeptides are also known in the art and these derivatives are typically reported to have improved properties relative to the naturally-occurring glycopeptides, including enhanced antibacterial activity. For example, U.S. patent application Ser. No. 09/847,042, filed May 1, 2001, describes various glycopeptide phosphonate derivatives, some of which contain an amino-containing side chain. Such phosphate derivatives are particularly useful as antibiotics for treating gram-positive infections.

Accordingly, a need exists for new efficient processes which are useful for preparing phosphonate derivatives of glycopeptide antibiotics having an amino-containing side chain.

SUMMARY OF THE INVENTION

The present invention provides novel processes for preparing phosphonate derivatives of glycopeptide antibiotics having an amino-containing side chain. Among other advantages, the first two steps of the present process are conducted in a single reaction vessel without isolation of the intermediate reaction products, thereby generating less waste and improving the overall efficiency and yield of the process compared to previous processes.

Specifically, in one of its aspects, this invention is directed to a process for preparing a compound of formula I:

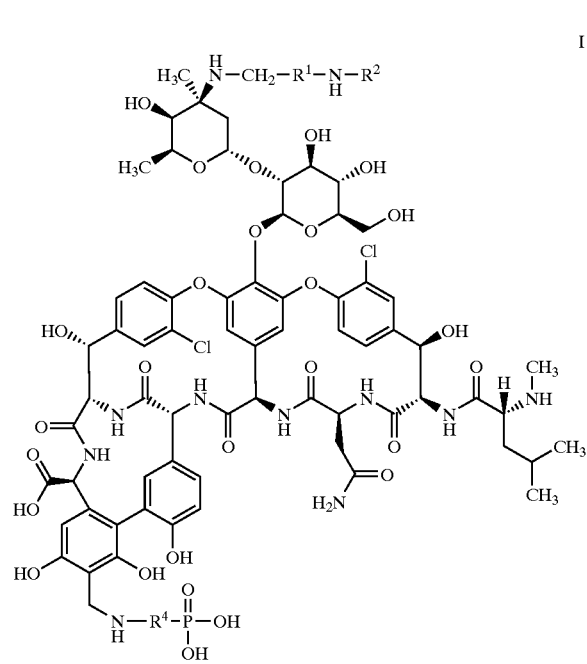

wherein $R^1$ is selected from the group consisting of $C_{1-10}$ alkylene, $C_{2-10}$ alkenylene and $C_{2-10}$ alkynylene;

$R^2$ is selected from the group consisting of $C_{1-20}$ alkyl, $C_{2-20}$ alkenyl, $C_{2-20}$ alkynyl, $C_{3-8}$ cycloalkyl, $C_{5-8}$ cycloalkenyl, $C_{6-10}$ aryl, $C_{2-9}$ heteroaryl, $C_{2-9}$ heterocyclic, $-R^a-Cy^1$, $-R^a-Ar^1-Ar^2$, $-R^a-Ar^1-R^b-Ar^2$, $-R^a-Ar^1-O-R^b-Ar^2$;

$R^4$ is $C_{1-10}$ alkylene;

$R^a$ is selected from the group consisting of $C_{1-10}$ alkylene, $C_{1-10}$ alkenylene and $C_{1-10}$ alkynylene;

$R^b$ is selected from the group consisting of $C_{1-6}$ alkylene, $C_{1-6}$ alkenylene and $C_{1-6}$ alkynylene;

$Cy^1$ is selected from the group consisting of $C_{3-8}$ cycloalkyl, $C_{5-8}$ cycloalkenyl, $C_{6-10}$ aryl, $C_{2-9}$ heteroaryl, $C_{2-9}$ heterocyclic;

$Ar^1$ and $Ar^2$ are independently selected from $C_{6-10}$ aryl and $C_{2-9}$ heteroaryl;

wherein each aryl, heteroaryl and heterocyclic group is optionally substituted with 1 to 3 substituents independently selected from the group consisting of $C_{1-6}$ alkyl, $C_{1-6}$ alkoxy, halo, hydroxy, nitro and trifluoromethyl, and each heteroaryl and heterocyclic group contains from 1 to 3 heteroatoms selected from nitrogen, oxygen or sulfur;

or a salt thereof;

the process comprising:

(a) reacting vancomycin or a salt thereof, with a compound of formula II:

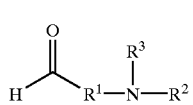

wherein $R^1$ and $R^2$ are as defined herein; and $R^3$ is a amine-labile protecting group; and a reducing agent to form a compound of formula III:

III

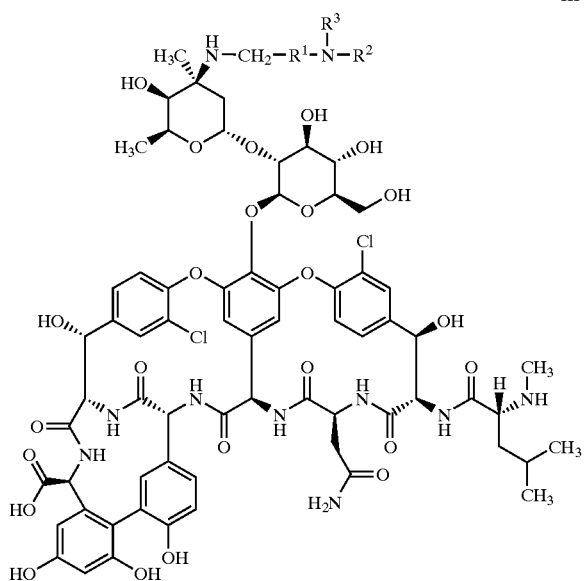

wherein $R^1$, $R^2$ and $R^3$ are as defined herein, or a salt thereof;

(b) reacting the compound of formula III with an amine to provide a compound of formula IV:

IV

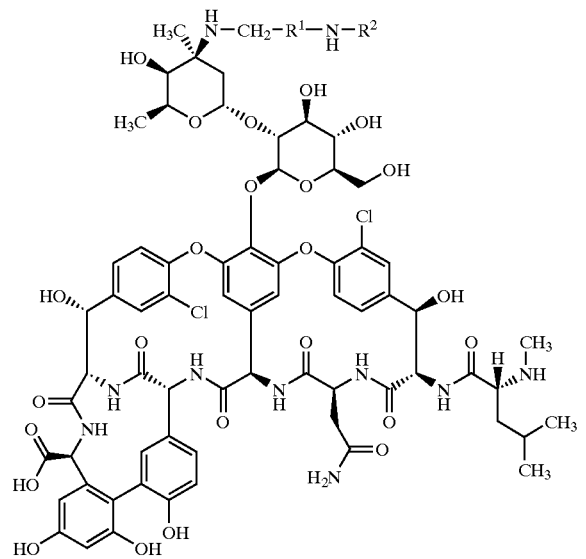

wherein $R^1$ and $R^2$ are as defined herein, or a salt thereof; wherein step (a) and step (b) are conducted in the same reaction mixture without isolation of the intermediate from step (a); and (c) reacting the compound of formula IV with formaldehyde and a compound of formula V:

V

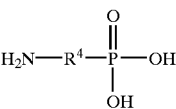

in the presence of a base to provide a compound of formula I, or a salt thereof.

In the above process, $R^1$ is preferably $C_{1-6}$ alkylene. More preferably, $R^1$ is $C_{1-2}$ alkylene. Still more preferably, $R^1$ is —$CH_2$—.

$R^2$ is preferably $C_{6-14}$ alkyl. More preferably, $R^2$ is $C_{8-12}$ alkyl. Still more preferably, $R^2$ is n-decyl.

In the process of this invention, $R^3$ is an amino-protecting group which is removed by treatment with an amine (i.e., a nucleophilic amine). Preferably, $R^3$ is a group of formula (A):

W—OC(O)— (A)

wherein W is selected from the group consisting of 9-fluorenylmethyl, 3-indenylmethyl, benz[f]inden-3-ylmethyl, 17-tetrabenzo[a,c,g,i]fluorenylmethyl, 2,7-di-tert-butyl[9-(10,10-dioxo-10,10,10,10-tetrahydrothioxanthyl)]methyl, 1,1-dioxobenzo[b]thiophene-2-ylmethyl, wherein the 9-fluorenylmethyl group is optionally substituted with 1 to 3 substitutents selected from the group consisting of $C_{1-6}$ alkyl, halo, nitro and sulfo.

Preferably, W is 9-fluorenylmethyl, wherein the 9-fluorenylmethyl group is optionally substituted with 1 to 3 substitutents selected from the group consisting of $C_{1-6}$ alkyl, halo, nitro and sulfo. More preferably, W is 9-fluorenylmethyl.

Preferably, $R^4$ is $C_{1-6}$ alkylene. More preferably, $R^4$ is $C_{1-4}$ alkylene. Still more preferably, $R^4$ is —$CH_2$—.

In step (a), the reducing agent is preferably an amine/borane complex. More preferably, the reducing agent is pyridine/borane or tert-butylamine/borane; and still more preferably, the reducing agent is tert-butylamine/borane.

In a preferred embodiment of this process, step (a) comprises the steps of:

(i) combining vancomycin or a salt thereof with a compound of formula II in the presence of base to form a reaction mixture;

(ii) acidifying the reaction mixture from step (i) with an acid; and (iii) contacting the reaction mixture from step (ii) with a reducing agent.

In this preferred embodiment, the base in step (i) is preferably a tertiary amine; more preferably, the base is diisopropylethylamine.

Preferably, the acid employed in step (ii) is trifluoroacetic acid or acetic acid.

In step (b), the amine employed is preferably ammonium hydroxide or a primary amine. More preferably, the amine is ammonium hydroxide, methylamine or tert-butylamine; and still more preferably, the amine is tert-butylamine.

In step (c), the base employed is preferably a tertiary amine. Preferably, the tertiary amine employed is diisopropylethylamine. In a preferred embodiment, the molar ratio of tertiary amine to compound of formula V is about 3:1 to about 5:1; more preferably, about 4:1.

DETAILED DESCRIPTION OF THE INVENTION

This invention relates to novel processes for preparing glycopeptide phosphonate derivatives having an amino-containing side chain. When describing such processes, the following terms have the following meanings, unless otherwise indicated.

Definitions

The term "alkyl" refers to a monovalent saturated hydrocarbon group which may be linear or branched. Unless otherwise defined, such alkyl groups typically contain from 1 to 20 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkenyl" refers to a monovalent unsaturated hydrocarbon group which may be linear or branched and which has at least one, and typically 1, 2 or 3, carbon-carbon double bonds. Unless otherwise defined, such alkenyl groups typically contain from 2 to 20 carbon atoms. Representative alkenyl groups include, by way of example, ethenyl, n-propenyl, isopropenyl, n-but-2-enyl, n-hex-3-enyl and the like.

The term "alkynyl" refers to a monovalent unsaturated hydrocarbon group which may be linear or branched and which has at least one, and typically 1, 2 or 3, carbon-carbon triple bonds. Unless otherwise defined, such alkynyl groups typically contain from 2 to 20 carbon atoms. Representative alkynyl groups include, by way of example, ethynyl, n-propynyl, n-but-2-ynyl, n-hex-3-ynyl and the like.

The term "alkylene" refers to a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "alkenylene" refers to a divalent unsaturated hydrocarbon group which may be linear or branched and which has at least one, and typically 1, 2 or 3, carbon-carbon double bonds. Unless otherwise defined, such alkenylene groups typically contain from 2 to 10 carbon atoms. Representative alkenylene groups include, by way of example, ethene-1,2-diyl, prop-1-ene-1,2-diyl, prop-1-ene-1,3-diyl, but-2-ene-1,4-diyl, and the like.

The term "alkynylene" refers to a divalent unsaturated hydrocarbon group which may be linear or branched and which has at least one, and typically 1, 2 or 3, carbon-carbon triple bonds. Unless otherwise defined, such alkynylene groups typically contain from 2 to 10 carbon atoms. Representative alkynylene groups include, by way of example, ethyne-1,2-diyl, prop-1-yne-1,2-diyl, prop-1-yne-1,3-diyl, but-2-yne-1,4-diyl, and the like.

The term "alkoxy" refers to a group of the formula —O—R, where R is alkyl as defined herein. Representative alkoxy groups include, by way of example, methoxy, ethoxy, n-propoxy, isopropoxy, n-butoxy, sec-butoxy, isobutoxy, tert-butoxy and the like.

The term "aryl" refers to a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like.

The term "cycloalkyl" refers to a monovalent saturated carbocyclic hydrocarbon group. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl and the like.

The term "cycloalkenyl" refers to a monovalent unsaturated carbocyclic hydrocarbon group having at least one carbon-carbon double bond in the carbocyclic ring. Unless otherwise defined, such cycloalkenyl groups typically contain from 5 to 10 carbon atoms. Representative cycloalkenyl groups include, by way of example, cyclopent-3-en-1-yl, cyclohex-1-en-1-yl and the like.

The term "halo" refers to fluoro, chloro, bromo and iodo; preferably, chloro, bromo and iodo.

The term "heteroaryl" refers to a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom.

The term "heterocycle" or "heterocyclic" refers to a monovalent saturated or unsaturated (non-aromatic) group having a single ring or multiple condensed rings and containing in the ring at least one heteroatom (typically 1 to 3 heteroatoms) selected from nitrogen, oxygen or sulfur. Unless otherwise defined, such heterocyclic groups typically contain from 2 to 9 total ring atoms. Representative heterocyclic groups include, by way of example, monovalent species of pyrrolidine, imidazolidine, pyrazolidine, piperidine, 1,4-dioxane, morpholine, thiomorpholine, piperazine, 3-pyrroline and the like, where the point of attachment is at any available carbon or nitrogen ring atom.

The term "vancomycin" is used herein in its art recognized manner to refer to the glycopeptide antibiotic known as vancomycin. See, for example, R. Nagarajan, "Glycopeptide Anitibiotics", Marcel Dekker, Inc. (1994) and references cited therein. The designation "$N^{van}$-" refers to substitution at the vancosamine nitrogen atom of vancomycin. This position is also referred to as the N3" position of vancomycin. Additionally, using a conventional vancomycin numbering system, the designation "29-" refers to the carbon atom position between the two hydroxyl groups on the phenyl ring of amino acid 7 (AA-7). This position is also sometimes referred to as the "7d" or the "resorcinol position" of vancomycin.

The term "salt" when used in conjunction with a compound referred to herein refers to a salt of the compound derived from an inorganic or organic base or from an inorganic or organic acid. Salts derived from inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like. Particularly preferred are citric, hydrobromic, hydrochloric, maleic, phosphoric, sulfuric and tartaric acids.

The term "protecting group" or "blocking group" refers to a group which, when covalently attached to a function group such as an amino, hydroxyl, thiol, carboxyl, carbonyl and the like, prevents the functional group from undergoing undesired reactions but which permits the function group to be regenerated (i.e., deprotected or unblocked) upon treatment of the protecting group with a suitable reagent. Representative protecting groups are disclosed, for example, in T. W. Greene and P. G. M. Wuts, "Protective Groups in Organic Synthesis" 3$^{rd}$ Ed., 1999, John Wiley and Sons, N.Y.

The term "amine-labile protecting group" refers to a protecting group which is removed upon treatment with a suitable amine.

Process Conditions

The process of the present invention is conducted in three steps beginning with vancomycin or a salt thereof. The first step of the process is a reductive alkylation step which involves first combining one equivalent of vancomycin or a salt thereof, with one or more equivalents of an aldehyde of formula II:

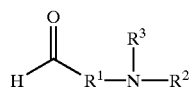

II wherein $R^1$, $R^2$ and $R^3$ are as defined herein to form a imine and/or hemiaminal intermediate in situ.

The aldehydes of formula II employed in the process of the present invention are well-known in the art and are either commercially available or can be prepared by conventional procedures using commercially available starting materials and conventional reagents. For example, see WO 00/39156, published on Jul. 6, 2000, which describes various methods for preparing such aldehydes.

Typically, the vancomycin or a salt thereof and the aldehyde are combined in an inert diluent in the presence of an excess amount of a suitable base to form a reaction mixture. Preferably, the inert diluent is N,N-dimethylformamide, N,N-dimethylacetamide, N-methylpyrrolidinone, acetonitrile/water, and the like or mixtures thereof. Preferably, from about 1 to about 2 equivalents of the aldehyde are employed; more preferably, about 1.1 to about 1.2 equivalents. In this reaction mixture, a mixture of imines and/or hemiaminals is believed to be formed between the aldehyde and the basic nitrogen atoms of vancomycin, i.e., the vancosamine nitrogen atom and the N-terminal (leucinyl) nitrogen atom.

Formation of the imine and/or hemiaminal intermediate is typically conducted at a temperature ranging from about 0° C. to about 75° C., preferably at ambient temperature (i.e., about 20–25° C.) for about 1 to about 24 hours, preferably for about 6 to 12 hours, or until formation of the imine and/or hemiaminal is substantially complete.

Any suitable base may be employed to neutralize the vancomycin salt and to facilitate formation of the imine and/or hemiaminal, including organic bases, such as amines, alkali metal carboxylate salt (i.e., sodium acetate and the like) and inorganic bases, such as alkali metal carbonates (i.e., lithium carbonate, potassium carbonate and the like). Preferably, the base is a tertiary amine including, by way of illustration, triethylamine, diisopropylethylamine, N-methylmorpholine, and the like. A preferred base is diisopropylethylamine. The base is typically employed in a molar excess relative to vancomycin. Preferably, the base is used in an amount ranging from about 1.5 to about 3 equivalents based on vancomycin; more preferably, about 1.8 to 2.2 equivalents.

When formation of the imine and/or hemiaminal mixture is substantially complete, the reaction mixture is acidified with an excess of acid. Any suitable acid may be employed including, by way of illustration, carboxylic acids (e.g. acetic acid, trichloroacetic acid, citric acid, formic acid, trifluoroacetic acid, methanesulfonic acid, toluenesulfonic acid and the like), mineral acids (e.g. hydrochloric acid, sulfuric acid, or phosphoric acid), and the like. Preferably, the acid is trifluoroacetic acid or acetic acid. The acid is typically added in a molar excess relative to vancomycin (and the base). Preferably, the acid is used in an amount ranging from about 3 to about 6 equivalents based on vancomycin; more preferably, about 3.5 to 5.5 equivalents.

While not wishing to be limited by theory, it is believed that the acid selectively hydrolyzes the imine and/or hemiaminal formed at the N-terminal amine of vancomycin in preference to the imine and/or hemiaminal formed at the vancosamine nitrogen atom. Acidification of the reaction mixture is typically conducted at a temperature ranging from about 0° C. to about 30° C., preferably at about 25° C., for about 0.25 to about 2.0 hours, preferably for about 0.5 to about 1.5 hours. Preferably, a polar, protic solvent is added during this step including, by way of example, methanol, ethanol, propanol, isopropanol, butanol, ethylene glycol, and the like. Alternatively, a mixed polar protic/non-protic solvent may be used, such as methanol/tetrahydrofuran, methanol/1,2-dimethoxyethane and the like After acidification, the reaction mixture is contacted with a reducing agent to reduce the imine and/or hemiaminal. Any suitable reducing agent can be employed which is compatible with the functionality present in the glycopeptide. For example, suitable reducing agents include sodium borohydride, sodium cyanoborohydride, zinc borohydride, sodium triacetoxyborohydride, pyridine/borane, tert-butylamine/borane, N-methylmorpholine/borane, ammonia/borane, dimethylamine/borane, triethylamine/borane, trimethylamine/borane, and the like. Preferred reducing agents are amine/borane complexes such as pyridine/borane and tert-butylamine/borane.

The reduction phase of the reaction is typically conducted at a temperature ranging from about 0° C. to about 30° C., preferably at about 25° C., for about 0.5 to about 24 hours, preferably for about 1 to about 6 hours, or until the reduction is substantially complete. Preferably, a polar, protic solvent is present during this reduction step. The polar, protic solvent is preferably added during the acidification described above.

In contrast to prior procedures, the product of the reductive alkylation process is not isolated but the reaction mixture is contacted with an amine to remove the protecting group (i.e., $R^3$) from the intermediate product. Any suitable amine may be used in this step of the process. Representative amines suitable for use include, by way of example, methylamine, ethylamine, tert-butylamine, triethylamine, piperidine, morpholine, ammonium hydroxide, 1,4-diazabicyclo[2.2.2]octane (DABCO) and the like. Preferred amines are methylamine, tert-butylamine, ammonium hydroxide and 1,4-diazabicyclo[2.2.2]octane.

This deprotection step is typically conducted at a temperature ranging from about 0° C. to about 60° C., preferably at about 40° C. to about 45° C., for about 2 to about 60 hours, preferably for about 3 to about 10 hours, or until the reaction is substantially complete. This step is typically conducted in an inert diluent, such as N,N-dimethylformamide, N,N-dimethylacetamide, N-methylpyrrolidinone, and the like. The resulting compound of formula IV is readily isolated and purified by conventional procedures, such as precipitation, filtration and the like.

In the next step of the process, the compound of formula IV is contacted with formaldehyde and a compound of formula V:

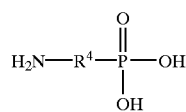

V wherein $R^4$ is as defined herein; in the presence of a base to provide a compound of formula I, or a salt thereof.

This step of the process is typically conducted by contacting one equivalent of compound IV or a salt thereof with one or more equivalents, preferably with about 2 to about 10 equivalents of a compound of formula V, and with an excess, preferably with about 4 to about 5 equivalents, formaldehyde in the presence of a base.

Phosphonate compounds of formula V are either commercially available or can be prepared by conventional procedures using commercially available starting materials and reagents. See for example, *Advanced Organic Chemistry*, Jerry March, 4th ed., 1992, John Wiley and Sons, New York, page 959; and Frank R. Hartley (ed.) *The Chemistry of Organophosphorous Compounds*, vol. 1–4, John Wiley and Sons, New York (1996). Aminomethylphosphonic acid is commercially available from Aldrich Chemical Company, Milwaukee, Wis.

The formaldehyde employed in this step of the process is typically added in an aqueous solution, for example, as a 37 wt. % solution in water optionally containing about 5 to about 15 wt. % methanol (i.e., Formalin).

Any suitable base may be used in this reaction including, for example, organic bases such as tertiary amines, and inorganic bases, such as alkali metal hydroxides (i.e., sodium hydroxide). Preferably, the base is a tertiary amine including, by way of example, triethylamine, diisopropylethylamine, and the like. A preferred tertiary amine is diisopropylethylamine. Preferably, the molar ratio of tertiary amine to compound V is about 3:1 to about 5:1; more preferably, about 3.5:1 to about 4.5:1; and still more preferably, about 4:1. Preferably, the pH of the reaction mixture is preferably about 10 to about 11.

Preferably, this reaction is conducted in an inert diluent, such as water, acetonitrile/water and the like. In a preferred embodiment, this step of the process is conducted in acetonitrile/water or water having v/v ratio ranging from about 3:2 to completely water.

This step of the process is typically conducted at a temperature ranging from about −20° C. to about 20° C., preferably at about −10° to about −5° C., for about 6 to about 48 hours, or until the reaction is substantially complete.

The resulting compound of formula I or a salt thereof is isolated by conventional procedures including, precipitation, filtration and the like. In a preferred isolation procedure, the pH of the reaction mixture is adjusted to about 2 to about 3 by addition of a suitable acid, such as aqueous hydrochloride acid. Preferably, the temperature of the reaction mixture is maintained below about 5° C. during acidification. Acetonitrile is then added to promote precipitation of the reaction product (i.e., a compound of formula I) and the resulting precipitate is collected by filtration and optionally washed with additional acetonitrile.

If desired, the reaction product can be further purified using reverse-phase HPLC or other chromatographic methods. In a preferred embodiment, the product is purified using a resin as described in co-pending U.S. application Ser. No. 10/226,676, filed on Aug. 23, 2002; which application claims the benefit of U.S. Provisional Application No. 60/314,712, filed on Aug. 24, 2001; the disclosures of which are incorporated herein by reference in their entirety.

Among other advantages, the process of the present invention provides for improved yield, purity and selectivity, i.e., reductive alkylation at the vancosamine amino group is favored over reductive alkylation at the N-terminus (e.g., the leucinyl group) by at least 10:1, more preferably 20:1. Additionally, because the reductive alkylation and deprotection steps are conducted in a single reaction vessel without isolation of the reaction intermediates, the process of the present invention is more efficient, provides a higher yield and generates less waste then previous processes.

The glycopeptide derivatives produced by the process of this invention are useful as antibiotics. See, for example, U.S. patent application Ser. No. 09/847,042, filed May 1, 2001; the disclosure of which is incorporated herein by reference in its entirety.

Additional details of the process of this invention are described in the following Examples which are offered to illustrate this invention and are not to be construed in any way as limiting the scope of this invention.

EXAMPLES

In the examples below, the following abbreviations have the following meanings. Any abbreviations not defined have their generally accepted meaning. Unless otherwise stated, all temperatures are in degrees Celsius (°C.).

DIPEA=diisopropylethylamine
DMF=N,N-dimethylformamide
DMSO=dimethyl sulfoxide
eq.=equivalent
Fmoc=9-fluorenylmethoxycarbonyl
TFA=trifluoroacetic acid In the following examples, vancomycin hydrochloride semi-hydrate was purchased from Alpharma, Inc. Fort Lee, N.J. 07024 (Alpharma AS, Oslo Norway). Other reagents and reactants are available from Aldrich Chemical Co., Milwaukee, Wis. 53201.

Example A

Preparation of N-Fmoc-Decylaminoacetaldehyde

Step A—Preparation of N-Fmoc-2-(n-Decylamino) ethanol 2-(n-Decylamino)ethanol (2.3 g, 11 mmol, 1.1 eq) and DIPEA (2.0 mL, 11 mmol, 1.1 eq) were dissolved in methylene chloride (15 mL) and cooled in an ice bath. 9-Fluorenylmethyl chloroformate (2.6 g, 10 mmol, 1.0 eq) in methylene chloride (15 ml) was added, the mixture stirred for 30 minutes then washed with 3 N hydrochloric acid (50 mL) twice and saturated sodium bicarbonate (50 mL). The organics were dried over magnesium sulfate, and the solvents removed under reduced pressure. N-Fmoc-2-(n-decylamino)ethanol (4.6 g, 11 mmol, 108%) was used without further purification.

Step B—Preparation of N-Fmoc-2-(n-Decylamino)acetaldehyde

To a solution of oxalyl chloride (12.24 mL) and methylene chloride (50 mL) at −35 to −45° C. was added DMSO (14.75 g) in methylene chloride (25 mL) over 20 minutes. The reaction mixture was stirred for 10 minutes at −35 to −45° C. A solution of N-Fmoc-2-(n-decylamino)ethanol (20.0 g) in methylene chloride (70 mL) was added over 25 minutes and then stirred 40 minutes at −35 to −45° C. Triethylamine (21.49 g) was then added and the mixture stirred for 30 minutes at −10 to −20° C. The reaction mixture was quenched with water (120 mL) followed by concentrated sulfuric acid (20.0 g) while maintaining the internal temperature at 0–5° C. The organic layer was isolated and washed with 2% sulfuric acid (100 mL) followed by water (2×100 mL). The organic solution was distilled under vacuum at 60° C. to about 100 mL. Heptane (100 mL) was added, the temperature of the oil bath raised to 80° C. and the distillation was continued until the residual volume was 100 mL. More heptane (100 mL) was added and the distillation repeated to a volume of 100 mL. The heating bath was replaced with a cold water bath at 15° C. The bath was cooled slowly to 5° C. over 20 minutes to start the precipitation of the product. The slurry was then cooled to −5 to −10° C. and the slurry was stirred for 2 hours. The solid was then collected on a Buchner funnel and washed with cold (−5° C.) heptane (2×15 mL). The wet solid was dried in vacuo to yield the title aldehyde.

Example 1

Preparation of $N^{van}$-2-(n-Decylamino)ethyl Vancomycin Hydrochloride

To a stirred mixture of 20 g (13.46 mmol) of vancomycin hydrochloride and 6.526 g (15.48 mmol) of N-Fmoc-2-(n-decylamino)acetyldehyde was added 130 mL of N,N-dimethylformamide and 4.7 mL (26.92 mmol) of N,N-diisopropylethylamine. The resulting mixture was stirred at room temperature under nitrogen for 15 hours, and 75 mL of methanol and 4.15 mL of trifluoroacetic acid (53.84 mmol) were added at 0° C. successively. The mixture was stirred for 1 hour and 1.93 mL (15.48 mmol) of borane-pyridine complex was added. The resulting mixture was stirred for 4 hours at 0° C., and 80 mL (161.52 mmol) of a 2 M methylamine in methanol was added. The resulting mixture was warmed to room temperature and stirred for 50 hours, cooled to 0° C., and water (350 mL) was added dropwise. The mixture was acidified to pH 3.60 by slow addition of 11 mL of concentrated hydrochloric acid, and precipitation occurred. The mixture was stirred for another 30 min and then it was filtered through a Buchner funnel. The resulting wet cake was washed with water (2×200 mL) and dried in vacuo for 16 hours to give 9.8 g of crude $N^{van}$-2-(n-decylamino)ethyl vancomycin hydrochloride. This intermediate may then be used in step (c) of the process as described in Example 3.

Example 2

Preparation of $N^{van}$-2-(n-Decylamino)ethyl Vancomycin Hydrochloride

To a 1L three-necked round bottom flask equipped with a mechanical stirrer, a thermometer and a nitrogen bubbler was added 180 mL of N,N-dimethylformamide (DMF). While stirring, 6.75 g (0.0160 mol) of N-Fmoc-2-(n-decylamino)-acetyldehyde and 25 g (0.0168 mol) of vancomycin hydrochloride were added successively. The addition funnel was rinsed with 20 mL of DMF; and then 5.85 mL (0.0336 mol) of N,N-diisopropylethylamine were added. The resulting mixture was stirred at room temperature under nitrogen for 6–8 hours while maintaining the temperature at 20–25° C. Methanol (95 mL) was added in one portion and then 5.2 mL (0.0672) of trifluoroacetic acid were added within 1 minute. The mixture was stirred for 0.25 hours and then 1.39 g (0.016 mol) of borane-tert-butyl amine complex were added to the reaction mixture in one portion. The addition funnel was rinsed with 5 mL of methanol, and the resulting mixture was stirred for 2 hours at, room temperature. tert-Butylamine (10.6 mL, 0.101 mol) was added in one portion and the resulting mixture was stirred at 40–42° C. for about 7 hours. The reaction mixture was then cooled to room temperature and 140 mL of 0.5 N HCl were added, followed by 600 mL o f a 10% brine solution at room temperature. The resulting mixture was stirred for 2 hours at 20–25° C., and then cooled to 10° C. and stirred for 1 hour. The resulting precipitate is collected using a 12.5 cm Buchner funnel by filtering the reaction mixture over a period of about 90 min. The wet cake was washed with cold water (2×50 mL) and sucked dry for 5 hours. The resulting material was added to 200 mL of acetonitrile while stirring to 2 hours at 20–25° C. The resulting slurry was filtered through an 8 cm Buchner funnel and the collected wet cake was washed with acetonitrile (2×25 mL) and dried under house vacuum (about 25 mm Hg) for 13 hours to afford 31.1 g of crude $N^{van}$-2-(n-decylamino)ethyl vancomycin hydrochloride. This intermediate may then be used in step (c) of the process as described in Example 3.

Example 3

Preparation of $N^{van}$-2-(n-Decylamino)ethyl 29-{[(Phosphonomethyl)amino]methyl}Vancomycin A 250 mL of three-necked round bottom flask equipped with a mechanical stirrer, a thermometer and a nitrogen outlet was charged with 5 g of $N^{van}$-2-(n-decylamino)ethyl vancomycin and 1.6 g of aminomethylphosphonic acid and 30 mL of acetonitrile. The slurry was stirred for 15 minutes to allow disperse solids at 20-30° C. and then 20 mL of water was added. The mixture was agitated for 15 minutes and 7.5 g of diisopropylethylamine was added. The resulting mixture was agitated until all solids dissolved. The reaction mixture was then cooled to −5 to −10° C. and 2.5 g of 3.7% aqueous formaldehyde was charged and the resulting mixture was agitated at −5 to −10° C. for 24 hours. The reaction was monitored by HPLC. After the reaction was complete, the reaction mixture was adjusted to pH 2–3 with 3M hydrochloric acid solution while maintaining the reaction temperature at −10 to 5° C. With moderate agitation, 125 mL of acetonitrile was added to the reaction mixture at 20 to 25° C. over 10 minutes. The resulting mixture was stirred at 20 to 25° C. for 2 hours and then filtered. The wet cake was washed with 20 mL of acetonitrile twice and dried for 18 hours in a vacuum oven at 20 to 25° C. to give 5.3 g of the title compound as a mixture of the di- and trihydrochloride salt in ~100% yield with a purity of ca. 80% (HPLC area) (i.e., a compound of formula I where $R^1$ is —$CH_2CH_2$—, $R^2$ is n-decyl and $R^4$ is —$CH_2$—).

Example 4

Preparation of $N^{van}$-2-(n-Decylamino)ethyl 29-{[(Phosphonomethyl)amino]methyl}Vancomycin To a 12-L jacketed three-necked flask equipped with a mechanical stirrer, nitrogen inlet and temperature probe was added 117 g (ca. 60 mmol) of $N^{van}$-2-(n-decylamino)ethyl vancomycin (ca. 80% purity). Aminomethylphosphonic acid (30 g, 320 mmol) was then added, followed by 420 mL of acetonitrile. The resulting slurry was stirred for 15 minutes and then 426 g of water was added and stirring continued for 15 minutes. Diisopropylethylamine (144 g, 1500 mmol) was added ant the mixture was stirred at room temperature for 1 hour. The resulting light pink solution was cooled to −7° C. (internal temperature) and 4.51 g (60 mmol) of 37% aqueous formaldehyde in 33 mL of acetonitrile were added. The resulting mixture was stirred at −7° C. (internal temperature) for 12 hours while monitoring the reaction by HPLC. After the reaction was complete (i.e., <1% starting material after 12 hours), the pH of the reaction mixture was adjusted from 10.4 to 2.59 by addition of 3 N aqueous hydrochloric acid solution while maintaining the internal reaction temperature at −4 to −5° C. The amount of 3 N aqueous hydrochloride acid used was 455 g. To the resulting mixture was added 3.1 kg of 95% ethanol at 5° C. and the mixture was stirred for 3 hours, and then filtered through a Buchner funnel. The resulting wet cake was washed with 500 g of ethyl acetate to give 135 g of a granular solid. This solid was dried at 30 mmHg at room temperature for 20 hours to give 116 g of the title compound as a mixture of the di- and trihydrochloride salt. Karl Fisher assay of this material showed an 11% water content; and HPLC analysis showed 1.7% unreacted glycopeptide and 3.6% bis-Mannich by product relative to the title compound.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A process for preparing a compound of formula I:

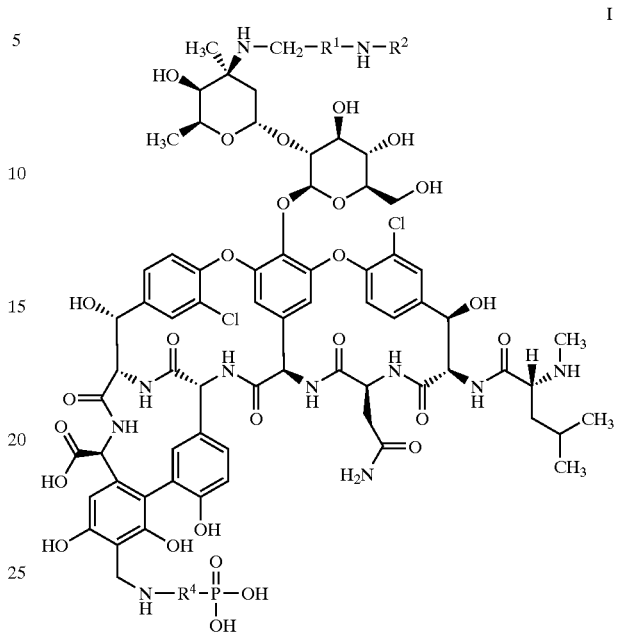

wherein
$R^1$ is selected from the group consisting of $C_{1-10}$ alkylene, $C_{2-10}$ alkenylene and $C_{2-10}$ alkynylene;
$R^2$ is selected from the group consisting of $C_{1-20}$ alkyl, $C_{2-20}$ alkenyl, $C_{2-20}$ alkynyl, $C_{3-8}$ cycloalkyl, $C_{5-8}$ cycloalkenyl, $C_{6-10}$ aryl, $C_{2-9}$ heteroaryl, $C_{2-9}$ heterocyclic, —$R^a$—$Cy^1$, —$R^a$—$Ar^1$—$Ar^2$, —$R^a$—$Ar^1$—$R^b$—$Ar^2$, —$R^a$—$Ar^1$—O—$R^b$—$Ar^2$;
$R^4$ is $C_{1-10}$ alkylene;
$R^a$ is selected from the group consisting of $C_{1-10}$ alkylene, $C_{1-10}$ alkenylene and $C_{1-10}$ alkynylene;
$R^b$ is selected from the group consisting of $C_{1-6}$ alklene, $C_{1-6}$ alkenylene and $C_{1-6}$ alkynylene;
$Cy^1$ is selected from the group consisting of $C_{2-8}$ cycloalkyl, $C_{5-8}$ cycloalkenyl, $C_{6-10}$ aryl, $C_{2-9}$ heteroaryl, $C_{2-9}$ heterocyclic;
$Ar^1$ and $Ar^2$ are independently selected from $C_{6-10}$ aryl and $C_{2-9}$ heteroaryl;
wherein each aryl, heteroaryl and heterocyclic group is optionally substituted with 1 to 3 substituents independently selected from the group consisting of $C_{1-6}$ alkyl, $C_{1-6}$ alkoxy, halo, hydroxy, nitro and trifluoromethyl, and each heteroaryl and heterocyclic group contains from 1 to 3 heteroatoms selected from nitrogen, oxygen or sulfur;
or a salt thereof;
the process comprising:
(a) reacting vancomycin or a salt thereof, with a compound of formula II:

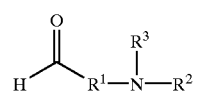

wherein R¹ and R² are as defined herein; and R³ is a amine-labile protecting group; and a reducing agent to form a compound of formula III:

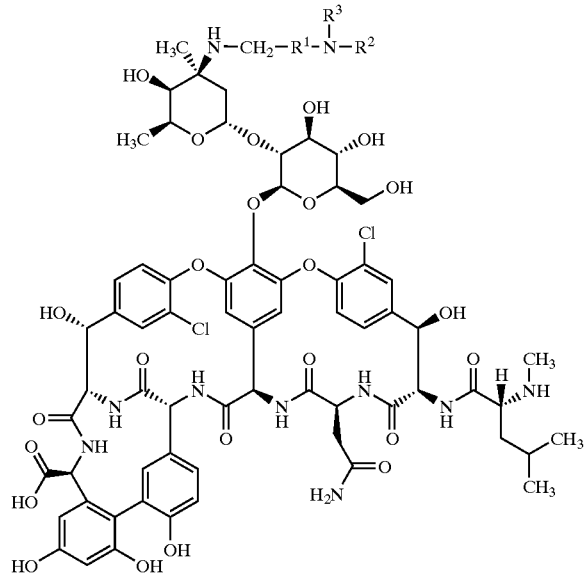

wherein R¹, R² and R³ are as defined herein, or a salt thereof;

(b) reacting the compound of formula III with an amine to provide a compound of formula IV:

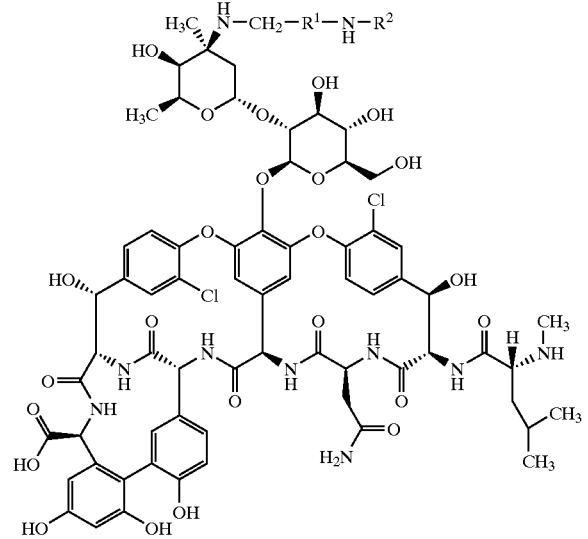

wherein R¹ and R² are as defined herein, or a salt thereof; wherein step (a) and step (b) are conducted in the same reaction mixture without isolation of the intermediate from step (a).

(c) reacting the compound of formula IV with formaldehyde and a compound of formula V:

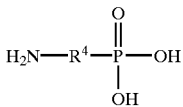

in the presence of a base to provide a compound of formula I, or a salt thereof.

2. The process according to claim 1, wherein R¹ is $C_{1-6}$ alkylene.

3. The process according to claim 2, wherein R¹ is —CH₂—.

4. The process according to claim 1, wherein R² is $C_{6-14}$ alkyl.

5. The process according to claim 4, wherein R² is n-decyl.

6. The process according to claim 1, wherein R³ is a group of formula (A):

W—OC(O)—          (A)

wherein W is selected from the group consisting of 9-fluorenylmethyl, 3-indenylmethyl, benz[f]inden-3-ylmethyl, 17-tetrabenzo[a,c,g,i]fluorenylmethyl, 2,7-di-tert-butyl[9-(10,10-dioxo-10,10,10,10-tetrahydrothioxanthyl)]methyl, 1,1-dioxobenzo[b]thiophene-2-ylmethyl, wherein the 9-fluorenylmethyl group is optionally substituted with 1 to 3 substitutents selected from the group consisting of $C_{1-6}$ alkyl, halo, nitro and sulfo.

7. The process according to claim 6, wherein W is 9-fluorenylmethyl, wherein the 9-fluorenylmethyl group is optionally substituted with 1 to 3 substitutents selected from the group consisting of $C_{1-6}$ alkyl, halo, nitro and sulfo.

8. The process according to claim 7, wherein W is 9-fluorenylmethyl.

9. The process according to claim 1, wherein R⁴ is $C_{1-6}$ alkylene.

10. The process according to claim 9, wherein R⁴ is —CH₂—.

11. The process according to claim 1, wherein the reducing agent in step (a) is amine/borane complex.

12. The process according to claim 11, wherein the reducing agent in step (a) is pyridine/borane or tert-butylamine/borane.

13. The process according to claim 1, wherein step (a) comprises the steps of:

(i) combining vancomycin or a salt thereof with a compound of formula II in the presence of base to form a reaction mixture;

(ii) acidifying the reaction mixture from step (i) with an acid; and (iii) contacting the reaction mixture from step (ii) with a reducing agent.

14. The process according to claim 13, wherein the base in step (i) is a tertiary amine.

15. The process according to claim 14, wherein the base in step (i) is diisopropylethylamine.

16. The process according to claim 13, wherein the acid in step (ii) is trifluoroacetic acid or acetic acid.

17. The process according to claim 1, wherein the amine in step (b) is ammonium hydroxide or a primary amine.

18. The process according to claim 17, wherein the amine in step (b) is ammonium hydroxide, methylamine or tert-butylamine.

19. The process according to claim 18, wherein the amine in step (b) is tert-butylamine.

20. The process according to claim 1, wherein the base in step (c) is a tertiary amine.

21. The process according to claim 20, wherein the base in step (c) is diisopropylethylamine.

22. The process according to claim 20, wherein the molar ratio of tertiary amine to compound of formula V is about 3:1 to about 5:1.

23. The process according to claim 22, wherein the molar ratio is about 4:1.

24. The process according to claim 1, wherein
$R^1$ is —$CH_2$—;
$R^2$ is n-decyl;
$R^3$ is W—OC(O)—, where W is 9-fluorenylmethyl;
$R^4$ is —$CH_2$—;
the reducing agent in step (a) is tert-butylamine/borane;
and the amine in step (b) is tert-butylamine.

* * * * *

UNITED STATES PATENT AND TRADEMARK OFFICE
CERTIFICATE OF CORRECTION

PATENT NO. : 6,979,723 B2
DATED : December 27, 2005
INVENTOR(S) : Leadbetter et al.

It is certified that error appears in the above-identified patent and that said Letters Patent is hereby corrected as shown below:

Column 14,
Line 42, "alklene" should read -- alkylene --; and
Line 44, "$C_{2-8}$ cycloalkyl" should read -- $C_{3-8}$ cycloalkyl --.

Signed and Sealed this

Fourth Day of April, 2006

JON W. DUDAS
*Director of the United States Patent and Trademark Office*